United States Patent [19]

Steiner et al.

[11] Patent Number: 5,068,413

[45] Date of Patent: Nov. 26, 1991

[54] PROCESS FOR THE PREPARATION OF CYCLIC AMINO ACIDS AND INTERMEDIATES USEFUL IN THE PROCESS

[75] Inventors: Klaus Steiner, Tannenweg; Wolfgang Herrmann, Zum Baumgarten; Günter Crone, Freiburg, all of Fed. Rep. of Germany; Charles S. Combs, Chester, N.J.

[73] Assignee: Godecke Aktiengesellschaft, Berlin, Fed. Rep. of Germany

[21] Appl. No.: 570,493

[22] Filed: Aug. 21, 1990

[30] Foreign Application Priority Data

Aug. 25, 1989 [DE] Fed. Rep. of Germany ....... 3928184

[51] Int. Cl.$^5$ ............................................ C07C 229/28

[52] U.S. Cl. ................................. 562/507; 558/303; 558/431; 558/432; 562/504

[58] Field of Search ................. 564/124, 126; 558/303, 558/431, 432; 562/504, 507

[56] References Cited

U.S. PATENT DOCUMENTS

| | | | |
|---|---|---|---|
| 4,024,175 | 5/1977 | Satzinger et al. | 260/514 |
| 4,087,544 | 5/1978 | Satzinger et al. | 424/305 |
| 4,894,476 | 1/1990 | Butler et al. | 562/504 |

*Primary Examiner*—Joseph Paul Brust
*Attorney, Agent, or Firm*—Francis J. Tinney

[57] ABSTRACT

Processes for the preparation of cyclic amino acid derivatives useful in the treatment of cerebral diseases such as epilepsy are disclosed. Novel intermediates useful in processes are also disclosed.

15 Claims, No Drawings

PROCESS FOR THE PREPARATION OF CYCLIC AMINO ACIDS AND INTERMEDIATES USEFUL IN THE PROCESS

BACKGROUND OF THE INVENTION

Gabapentin is a generic term used to identify the chemical compound (1-aminomethyl)-1-cyclohexaneacetic acid.

$$H_2N-CH_2-C-CH_2-COOH$$
$$(CH_2)_5$$

It is useful in therapy of certain cerebral disorders such as certain forms of epilepsy, faintness attacks, hypokinesis and cranial traumas. U.S. Pat. Nos. 4,024,175 and 4,087,544 cover the compound and its uses. They also disclose an acid salt, i.e. gabapentin hydrochloride hydrate in a ratio of 4:4:1 and a sodium salt of gabapentin hydrate in a ratio of 2:1. These patents are hereby incorporated by reference.

The patents describe various processes for the preparation of this and similar compounds of general formula

$$H_2N-CH_2-C-CH_2-COOR_1$$
$$(CH_2)_n$$

wherein $R_1$ is a hydrogen atom or a lower alkyl radical and n is 4, 5, or 6 and the pharmaceutically acceptable salts thereof, which depend upon known methods used for the preparation of primary amines or amino acids.

All examples of the syntheses end in an isocyanate or urethane that can easily be converted into the desired (1-aminomethyl)-1-cyclohexaneacetic acid by acidic hydrolysis (preferred) to give an acid or basic hydrolysis to give a basic salt or followed by acidification to give an acid salt.

U.S. Pat. No. 4,894,476 covers crystalline gabapentin monohydrate and methods for producing the same. This patent is hereby incorporated by reference.

DETAILED DESCRIPTION OF THE INVENTION

The present invention is concerned with a process for the preparation of cyclic amino acid derivatives of formula

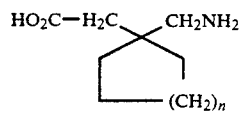

in which n is 1, 2 or 3 and preferably 2, and of the pharmacologically acceptable salts thereof.

The process for the preparation comprises converting a malonic ester derivative of formula

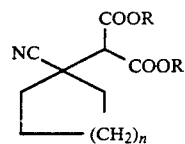

in which R is an alkyl radical containing up from 1 to 5 carbon atoms and preferably an ethyl radical and n has the above meaning, by alkaline hydrolysis into a cyanocycloalkylmalonic acid derivative of the formula

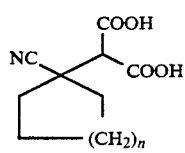

in which n has the above meaning. This is then decarboxylated either directly (Scheme II) or via an intermediate (Scheme I) of the formula

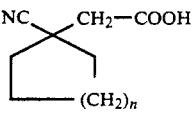

in which n has the above meaning, and the nitrile group is hydrogenated in the presence of a catalyst. The lactam of formula

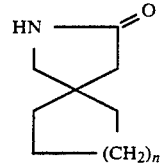

in which n has the above meaning, is formed as a main product or as a by-product, and is then optionally separated off the compound of formula (I) and converted by hydrolysis into a compound of formula (I) or a desired salt thereof.

A compound of formula (I) in which n is 2 (gabapentin, Drugs of the Future, Vol. 9, No. 6, pp. 418–419/1984) is well known. Starting from cyclohexanone, it was prepared by a laborious 7- or 8-step synthesis.

Known processes for the preparation of gabapentin include a synthesis intermediate which must be converted into gabapentin hydrochloride by acid hydrolysis in an aqueous medium. By splitting off water and intramolecular cyclization, there is formed from gabapentin a lactam (2-aza-spiro-[4,5]decan-3-one) of formula V. The gabapentin hydrochloride obtained must then be converted into gabapentin in dilute aqueous solution by means of an ion exchanger. The gabapentin can then be obtained from the aqueous solution without appreciable lactam formation by means of technically laborious methods. The laboriousness of the synthesis, the undesired lactam formation, as well as the laborious isolation of gabapentin from aqueous solutions consequently give rise to a high cost of preparation for gabapentin.

It is an object of the present invention to provide an economical process for the preparation of compounds of formula (I) and especially of gabapentin which can be carried out on a large scale. The number of synthesis steps needs to be reduced and the undesired formation of lactam needs to be suppressed. Furthermore, a process is needed which permits the isolation of gabapentin from nonaqueous solutions.

Surprisingly, it has been found that the problem was solved by the reaction steps described above and in the instant claims. After the almost quantitative conversion of the malonic acid ester derivatives (II) by alkaline hydrolysis into the 1-cyanocycloalkylalonic acid derivatives (III) and by gentle decarboxylation into the 1-cyanocycloalkylacetic acid derivatives (IV), these can be hydrogenated in alcoholic solvents by means of catalysts to give the compounds of formula (I) directly. By means of the reaction conditions of the present invention, the formation of a lactam of formula (V) can thereby be prevented. In this new process, the conversion of salts of formula (I) into the corresponding bases, as well as the laborious isolation of the latter from aqueous solutions (see the following Scheme I). The process according to the present invention is illustrated by the following reaction Scheme I.

Scheme I

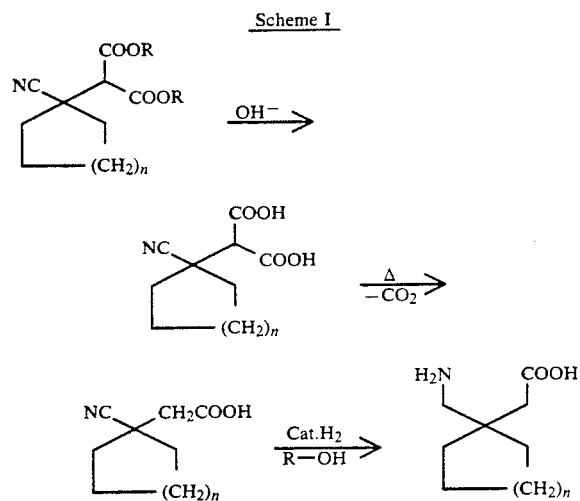

Raney nickel, Raney cobalt or noble metal catalysts, for example rhodium or palladium, optionally in a carrier, such as carbon are used.

Surprisingly, it has been found that cyanocycloalkylmalonic acid derivatives of formula (III) can, in the case of the catalytic hydrogenation at an elevated temperature, with the splitting off of carbon dioxide, be converted into a cyclic lactam of formula (V). This lactam can be converted by acid hydrolysis into the desired end product (I) according to the following Scheme II.

Scheme II

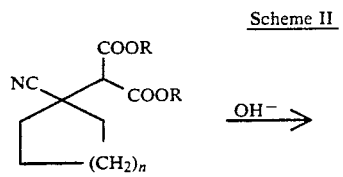

-continued
Scheme II

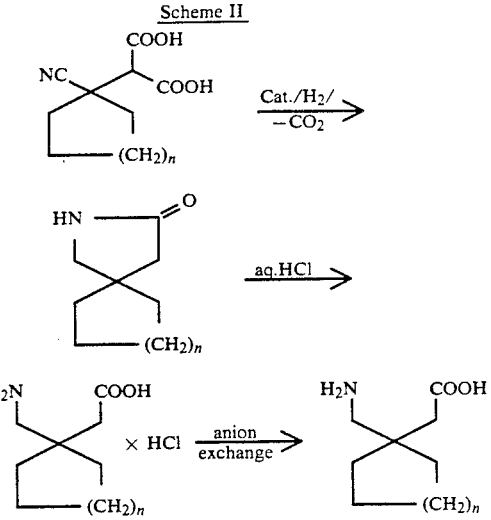

The alkaline hydrolysis of the compounds (II), and the conversion thereof into cyanocycloalkylmalonic acid derivatives of formula (III) usually takes place either by means of alkali metal or alkaline earth metal hydroxides or by means of salts thereof with weak acids, for example acetic acid or carbonic acid.

Raney nickel, Raney cobalt or noble metals, for example platinum, palladium or rhodium, optionally on conventional carrier materials are used. The hydrolysis of the compounds (V) takes place by means of strong mineral acids, for example hydrochloric acid or sulfuric acid.

The decarboxylation of compounds of formula (III) takes place either in the melt or in an organic solvent, for example ethyl acetate, toluene, methyl ethyl ketone, dioxane or hexane, an alcohol containing up to eight carbon atoms or a halogenated hydrocarbon, for example 3,3-trichloroethylene. The alkaline hydrolysis of the compounds (II) is preferably carried out in an alcohol containing up to four carbon atoms or in a mixture thereof with water.

The hydrogenation of compounds (III) and (IV) is carried out at a pressure of 1 to 50 KPa and in a relatively wide temperature range of from ambient temperature to 80° C. if the hydrogenation starts from compounds (IV). If, on the other hand, compounds (III) are used as starting materials with the inclusion of the decarboxylation and avoidance of the intermediate (IV), the temperatures under the same pressure conditions are preferably higher and are in the range of 50 to 120° C. The alcohol used is preferably ethanol, isopropanol or butanol.

The following examples are given for the purpose of illustrating the present invention and are not intended to limit the scope in any way.

EXAMPLE 1

(1-Cyanocyclohexyl)-malonic acid 50 g Diethyl (1-cyanocyclohexyl)-malonate are dissolved in 175 mL methanol at 40° C. At this temperature, a solution of 29.9 g sodium hydroxide in 150 mL water is added dropwise. The reaction mixture is stirred for 30 minutes at 40° C. After cooling to 20° C., the precipitated product (sodium salt) is filtered off with suction, the filter cake is washed with 50 mL methanol and the product is dried at 60° C. to constant weight. The product is dissolved in 500 mL of water at 10° C., and adjusted to a pH of one to two at 10-15° C. with concentrated hydrochloric acid. The substance which precipitates out is extracted three times with, in each case, 300 mL ethyl acetate. The combined ethyl acetate phases are dried and evaporated on a rotary evaporator at 35° C. The white residue obtained is dried to constant weight at 35° C. in a vacuum drying cabinet. 35.5 g of the title compound are obtained (89.8% of theory); m.p. 99.9° C.

EXAMPLE 2

(1-Cyanocyclohexyl)-acetic acid 35.5 g (1-Cyanocyclohexyl)-malonic acid are suspended in 400 mL toluene and heated, while stirring, for about one hour to 80-85° C. In the course of the decarboxylation, an almost clear solution is obtained. After filtration, the toluene is distilled off in a vacuum at 35° C. The crude product is dissolved in a saturated aqueous solution of sodium bicarbonate and stirred with ethyl acetate. After separating off the organic phase, the aqueous phase is acidified with concentrated hydrochloric acid, while cooling with ice to 5° C. The solid product which precipitates out is filtered off with suction and then washed with water. The filter cake is dissolved in ethyl acetate and the solution dried over anhydrous sodium sulphate. After filtration, the ethyl acetate is evaporated on a rotary evaporator at 35° C. The residue is dried to constant weight in a vacuum drying cabinet at 35° C. 19.6 g of the title compound are obtained (70% of theory); m.p. 102° C.

EXAMPLE 3

Gabapentin

A solution of 3 g (1-cyanocyclohexyl)-acetic acid in 10.5 mL methanol is hydrogenated at 10 bar hydrogen pressure and 30° C. in the presence of rhodium-carbon (5%) over a period of five hours. The reaction mixture is filtered and the filtrate evaporated on a rotary evaporator at 30° C. The crystalline residue is stirred with isopropanol and the crystallizate is filtered off with suction and dried to constant weight in a vacuum drying cabinet at 30° C. 2.0 g of the title compound are obtained (65.2% of theory); m.p. 152° C.

EXAMPLE 4

Gabapentin hydrochloride

A solution of 10 g (1-cyanocyclohexyl)-malonic acid in 200 mL ethanol is hydrogenated at 10 bar hydrogen pressure and 90° C. in the presence of 4 g Raney nickel for five hours. The reaction mixture is filtered and the filtrate is evaporated to dryness on a rotary evaporator. The residue is taken up in 170 mL 25% hydrochloric acid and boiled under reflux for 24 hours. The reaction mixture is then evaporated on a rotary evaporator and the evaporation residue is stirred in 100 mL acetone, cooled to 4° C. and filtered off with suction. The filter cake is further washed with a little cooled acetone and the residue is dried to constant weight at 70° C.. 5.6 g of the title compound are obtained (56.9% of theory); m.p. 124° C.

EXAMPLE 5

1-(Aminomethyl)-cyclohexane-acetic acid hydrochloride 22.3 l of water and 22.3 l of concentrated hydrochloric acid are mixed in a T100 reactor and 6.41 kg gabapentin lactam added thereto, while stirring. The clear brown solution formed is subsequently boiled under reflux for six hours at 108° C. and the reaction mixture is left to stand until it has cooled to 28° C.. The white precipitate obtained is again dissolved by the addition of a further 40 l of water. For the removal of still undissolved lactam, the reaction mixture is extracted three times with, in each case, 30 l dichloromethane. The pale yellow aqueous phase is evaporated to dryness in a vacuum evaporator (QVF 100 L), the temperature finally reaching to 80° C. at 133 Pa. The almost dry crystal mass is stirred in 12.8 l acetone and filtered off with suction. It is then washed with 2 l acetone and dried for four hours at 60° C. The yield is about 60% of theory.

EXAMPLE 6

1-(Aminomethyl)-cyclohexaneacetic acid

A 3 m long and 20 mm wide chromatography column is filled with 50 l of an ion exchanger resin (IRA 68). The resin is regenerated with a solution of 14 l concentrated aqueous ammonia in 300 l demineralized water and subsequently washed with 150 l demineralized water. As soon as the eluate has reached pH 6.8 and no more chloride can be detected, a solution of 8.67 kg (40.8 mole) 1-aminomethyl-1-cyclohexaneacetic acid hydrochloride in 43 l demineralized water is added to the column. The free amino acid is eluted with demineralized water at a rate of 1.5 l/min and collected in 15 fractions of 15 l. The combined fractions are evaporated at 6.65 Pa and at most 45° C. The solid white residue is introduced into 20 l methanol, heated to reflux, filtered and cooled to − 10° C. The product which crystallizes out is centrifuged off, washed with 10 l cold methanol and dried for 17 hours at 30-40° C. 4.9 kg (71% of theory) of pure 1-(aminomethyl)-cyclohexaneacetic acid are obtained; m.p. 165° C. A further 0.8 kg can be obtained by working up the mother liquors.

We claim:

1. A process for the preparation of a compound formula

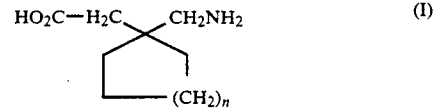

or a pharmaceutically acceptable salt thereof, wherein n is an integer of from 1 to 3 comprising:

(a) converting a malonic ester of formula

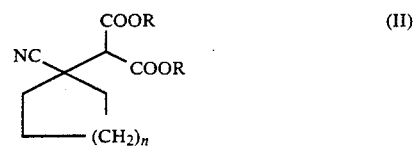

wherein R is an alkyl of from 1 to 5 carbon atoms and n is as described above by alkaline hydrolysis into a cyanocycloalkylmalonic acid derivative of formula

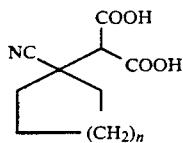 (II)

(b) diacarboxylating gently the cyanocycloalkylmalonic acid of step (a) to produce a 1-cyanocycloalkylacetic acid of formula

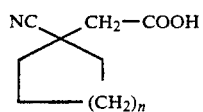 (IV)

(c) hydrogenating the acetic acid from step (b) in an alkanol solvent using a catalyst to produce a compound of formula I above.

2. A process according to claim 1, wherein in step (c) the catalyst is selected from Raney nickel, Raney cobalt or noble metal catalysts.

3. A process according to claim 1, wherein in step (b) the temperature is from about ambient to about 80° C. at a pressure of from about 1 to 50 KPa.

4. A process according to claim 1, wherein in step (c) the alcohol solvent is ethanol, isopropanol or butanol.

5. A process according to claim 1, wherein in step (b) decarboxylation takes place in the melt.

6. A process according to claim 1, wherein in step (b) decarboxylation takes place in an organic solvent.

7. A process according to claim 6, wherein the organic solvent is ethyl acetate, toluene, methyl ethyl ketone, dioxane, hexane, an alkanol of from 1 to integer 6 carbon atoms or a halogenated hydrocarbon.

8. A process according to claim 1, wherein in step (a) alkaline hydrolysis is carried out in an alkanol of from 1 to 4 carbon atoms or a mixture of the alkanol and water.

9. A process according to claim 1, wherein the product formed is gabapentin.

10. A process according to claim 1, wherein said compound of formula I is converted to a pharmaceutically acceptable salt.

11. A process for the preparation of a compound formula

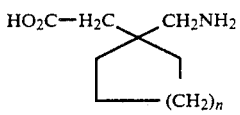 (I)

or a pharmaceutically acceptable salt thereof, wherein n is an integer of from 1 to 3 comprising:
(a) catalytic hydrogenation at an elevated temperature of a cyanocycloalkylmalonic acid of the formula

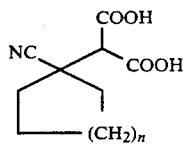 (II)

wherein n is as described above, to a cyclic lactam of the formula

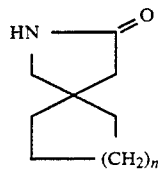 (V)

wherein n is as described above, and
(b) the lactam of formula V is converted by acid hydrolysis to a compound of formula I.

12. A process according to claim 11, wherein said compound of formula I is converted to a pharmaceutically acceptable salt.

13. A process according to claim 11, wherein the hydrogenation is carried out at a pressure of from 1 to 50 KPa at a temperature of from about 50-120° C.

14. A process according to claim 11, wherein the hydrogenation catalyst is selected from Raney nickel, Raney cobalt or platinum, palladium, or rhodium.

15. A process according to claim 11, wherein the acid hydrolysis of the lactam utilizes hydrochloric acid or sulfuric acid.

* * * * *

UNITED STATES PATENT AND TRADEMARK OFFICE
CERTIFICATE OF CORRECTION

PATENT NO. : 5,068,413

DATED : November 26, 1991

INVENTOR(S) : Steiner, et al

It is certified that error appears in the above-identified patent and that said Letters Patent is hereby corrected as shown below:

Column 7, line 11, delete "diacarboxylating" and insert --decarboxylating--.

Signed and Sealed this

Thirtieth Day of March, 1993

Attest:

STEPHEN G. KUNIN

Attesting Officer

Acting Commissioner of Patents and Trademarks